(12) United States Patent
Vickers et al.

(10) Patent No.: US 8,653,029 B2
(45) Date of Patent: Feb. 18, 2014

(54) FLOWABLE PASTE AND PUTTY BONE VOID FILLER

(75) Inventors: Scott Mitchell Vickers, Hernando, MS (US); Jeffrey L. Scifert, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 259 days.

(21) Appl. No.: 12/512,651

(22) Filed: Jul. 30, 2009

(65) Prior Publication Data

US 2011/0028393 A1 Feb. 3, 2011

(51) Int. Cl.
| | |
|---|---|
| *A61K 38/18* | (2006.01) |
| *A61K 8/73* | (2006.01) |
| *A61K 9/14* | (2006.01) |
| *A61P 19/08* | (2006.01) |
| *A61F 2/28* | (2006.01) |

(52) U.S. Cl.
USPC ......... 514/8.8; 514/7.6; 514/16.7; 424/70.13; 424/488; 424/602; 623/23.61

(58) Field of Classification Search
None
See application file for complete search history.

(56) References Cited

U.S. PATENT DOCUMENTS

| | | | |
|---|---|---|---|
| 4,624,255 | A | 11/1986 | Schenck et al. |
| 4,863,457 | A | 9/1989 | Lee |
| 5,522,844 | A | 6/1996 | Johnson |
| 5,868,789 | A | 2/1999 | Huebner |
| 6,069,129 | A | 5/2000 | Sandberg et al. |
| 6,179,862 | B1 | 1/2001 | Sawhney |
| 6,287,588 | B1 | 9/2001 | Shih et al. |
| 6,331,311 | B1 | 12/2001 | Brodbeck et al. |
| 6,428,804 | B1 | 8/2002 | Suzuki et al. |
| 6,432,063 | B1 | 8/2002 | Marcus |
| 6,461,631 | B1 | 10/2002 | Dunn et al. |
| 6,491,651 | B1 | 12/2002 | Leahy et al. |
| 6,589,549 | B2 | 7/2003 | Shih et al. |
| 6,595,388 | B2 | 7/2003 | Mizutani et al. |
| 6,630,155 | B1 | 10/2003 | Chandrashekar et al. |
| 6,632,457 | B1 | 10/2003 | Sawhney |
| 6,696,073 | B2 | 2/2004 | Boyce et al. |
| 6,756,058 | B2 | 6/2004 | Brubaker et al. |
| 6,773,714 | B2 | 8/2004 | Dunn et al. |
| 6,863,694 | B1 | 3/2005 | Boyce et al. |
| 6,911,212 | B2 | 6/2005 | Gertzman et al. |
| 6,974,462 | B2 | 12/2005 | Sater |

(Continued)

FOREIGN PATENT DOCUMENTS

WO 03005961 A2 1/2003

OTHER PUBLICATIONS

Cohen et al., Calcium phosphate bone cement—the Norian skeletal repair system in orthopedic surgery. AORN Journal , May 1997, 7 pages.
U.S. Appl. No. 12/194,432, filed Aug. 19, 2008.

(Continued)

*Primary Examiner* — Xiaozhen Xie
(74) *Attorney, Agent, or Firm* — William D. Schmidt; Sorell, Lenna & Schmidt, LLP

(57) ABSTRACT

The present invention provides a composition that may be used as an implant or a bone graft substitute or extender for filling voids and/or promoting fusion of osseous tissues. The implant may comprise ceramic granules such as calcium phosphate granules and one or more polysaccharide excipients, and may be in the form of a putty or flowable paste. Optionally, the implant may also comprise a growth factor such as a bone morphogenetic protein.

17 Claims, 5 Drawing Sheets

(56) References Cited

U.S. PATENT DOCUMENTS

| | | |
|---|---|---|
| 7,019,192 B2 | 3/2006 | Gertzman et al. |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,318,840 B2 | 1/2008 | McKay |
| 7,329,259 B2 | 2/2008 | Cragg |
| 7,361,168 B2 | 4/2008 | Makower et al. |
| 7,367,978 B2 | 5/2008 | Drewry et al. |
| 7,393,405 B2 | 7/2008 | Bohner |
| 7,449,019 B2 | 11/2008 | Uchida et al. |
| 7,459,018 B2 | 12/2008 | Insley et al. |
| 7,462,155 B2 | 12/2008 | England |
| 7,473,312 B2 | 1/2009 | Barralet et al. |
| 7,482,174 B2 | 1/2009 | Kiefer et al. |
| 7,494,950 B2 | 2/2009 | Armitage et al. |
| 2002/0055143 A1* | 5/2002 | Bell et al. ............ 435/69.1 |
| 2003/0180376 A1* | 9/2003 | Dalal et al. ............ 424/602 |
| 2008/0019969 A1 | 1/2008 | Gorman |
| 2008/0019970 A1 | 1/2008 | Gorman |
| 2008/0019975 A1 | 1/2008 | Gorman |
| 2008/0031914 A1* | 2/2008 | Drapeau et al. ........ 424/423 |
| 2008/0091207 A1 | 4/2008 | Truckai et al. |
| 2008/0147197 A1 | 6/2008 | Mckay |
| 2008/0175911 A1 | 7/2008 | Mckay et al. |
| 2008/0213283 A1 | 9/2008 | Olmarker et al. |
| 2008/0294261 A1 | 11/2008 | Pauza et al. |
| 2008/0317805 A1 | 12/2008 | Mckay et al. |
| 2009/0024135 A1 | 1/2009 | Triplett et al. |
| 2009/0028960 A1 | 1/2009 | Leonard et al. |
| 2009/0142385 A1* | 6/2009 | Gross et al. .......... 424/422 |
| 2009/0246244 A1* | 10/2009 | McKay et al. .......... 424/423 |

OTHER PUBLICATIONS

U.S. Appl. No. 12/193,794, filed Aug. 19, 2008.

* cited by examiner

FLOWABLE PASTE AND PUTTY BONE VOID FILLER

BACKGROUND

Bone defects may be caused by a number of different factors, including but not limited to trauma, pathological disease or surgical intervention. Because bone provides both stability and protection to an organism, these defects can be problematic. In order to address these defects, compositions that contain both natural and synthetic materials have been developed. These compositions may, depending upon the materials contained within them, be used to repair tissues and to impart desirable biological and/or mechanical properties.

Among the known bone repair materials and bone void fillers is autologous cancellous bone. This type of bone has the advantage of being both osteoinductive and non-immunogenic. Unfortunately, this type of bone is not available under all circumstances. Moreover, donor site morbidity and trauma add to the limitations of autologous cancellous bone. One alternative to autologous bone is allograft bone. Unfortunately, allograft bone has a lower osteogenic capacity than autograft bone, has a high resorption rate, creates less revascularization at the bone defect site, typically induces a greater immunogenic response and may result in the transfer of certain diseases.

In order to avoid the issues that attach to the use of autologous and allograft bone, one may use synthetic materials. However, known synthetic materials suffer from one or more of the following drawbacks, including unacceptable workability, handling and setting parameters; insufficient density; undesirable absorption rates; and an inability to impart adequate stability.

Accordingly, there is a need for new defect fillers that have desired levels of one or more of the following: stability, rate of absorption, workability and cohesiveness. When within the defect filler these parameters are at desired levels, a healthcare provider can adequately manipulate the defect filler into a desired shape and appropriately rely on it to be stable in the void for a sufficient amount of time while promoting bone growth.

SUMMARY

In some embodiments, an implant is provided that may be used as a bone graft substitute or extender for filling osseous voids and/or for promoting fusion of osseous tissue.

According to one embodiment, there is a composition for filling an osseous void comprising a one or more polysaccharide excipients; and a plurality of ceramic granules, the composition being moldable and adaptable to fill an osseous void on implantation, wherein the composition remains moldable after implantation. The composition may be in the form of a flowable paste or a putty.

According to another embodiment, there is a composition for filling an osseous void comprising a flowable putty comprising of one or more polysaccharide excipients; and a plurality of ceramic granules. The composition may also comprise one or more growth factors.

Among the advantages in some of the embodiments are that the composition has an increased cohesiveness and may be molded to the shape of the osseous void. This cohesiveness renders the material advantageous in procedures in which an implant is to be manipulated and packed into a site. Furthermore, because the implants are stable and not rapidly absorbed, they may provide scaffoldings for bone growth.

DETAILED DESCRIPTION

Figure 1:
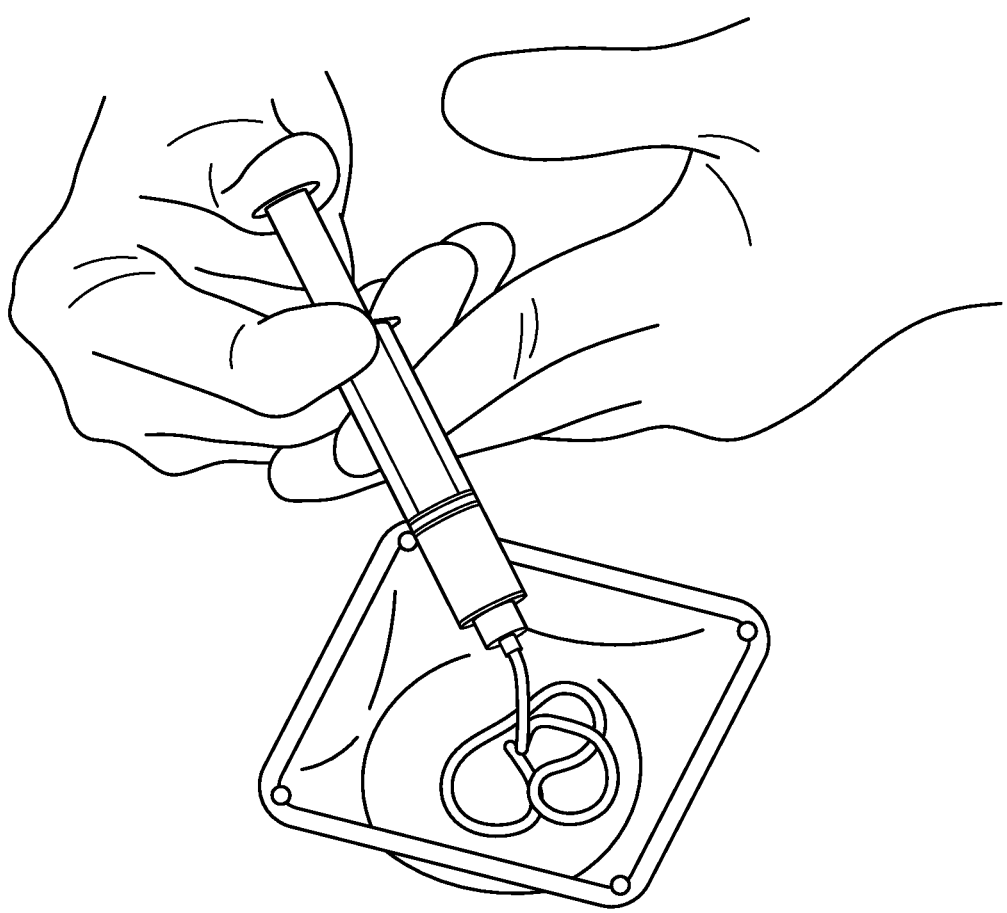
FIG. 1 is a representation of a person dispensing the flowable composition of an embodiment of the present invention through a tube.

Unless defined otherwise, all technical and scientific terms used herein have the same meaning as is commonly understood by one of ordinary skill in the art to which this invention belongs. For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth are reported as precisely as possible. Any numerical value, however, inherently contains certain errors necessarily resulting from the standard deviation found in its respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

The compositions of the present invention may, for example, be used as a bone graft substitute or extender for filling osseous voids and/or promoting fusion of osseous tissues.

According to one embodiment, there is a composition that comprises, consist essentially of or consist of polysaccharides and granules. The polysaccharides may for example comprise, consist essentially of or consist of alginates. The granules may for example be ceramic materials.

According to another embodiment there is an implant for filling an osseous void comprising one or more polysaccharide excipients; and a plurality of ceramic granules. In some embodiments, a bioactive agent such as a growth factor is also present.

The polysaccharides may for example form a flowable putty. In some embodiments, the polysaccharides are non-cross-linked alginates. In some embodiments, medium grade alginates are used. In some embodiments, the polysaccharide is chitosan or a mixture of chitosan and alginates. Additionally, the composition may be selected to so that it has a flowable state or a doughy state.

In some embodiments, the viscosity of the composition is similar to that of Play-doh®. The viscosity of the material may be controlled by the relative proportions of the components and the size of the granules. For example, increasing the amount of alginate will cause the composition to be more viscous, i.e. less flowable. Similarly, increasing the average particle size of the granules will cause the composition to be more viscous. As a composition becomes more viscous, it may be more putty-like. Similarly, as a composition becomes less viscous, it may be described as a flowable material. However, as a person of ordinary skill in the art would be aware, the states of being "flowable" or "putty-like" exist along a continuum.

The granules may for example be in the form of beads. Additionally, the granules, regardless of whether they are in the form of beads, may be regularly and/or irregularly shaped ceramic materials and may be comprised of, consist essentially of, or consist of calcium phosphate. The calcium phosphate may, for example, be biphasic calcium phosphate. A non-limiting example of the biphasic calcium phosphate may consist of about 15 percent hydroxyapatite and about 85 percent beta-tricalcium phosphate. Other examples of calcium phosphate materials that may be used in connection with the present invention include but are not limited to tetra-calcium phosphate, di-calcium phosphate, tri-calcium phosphate, mono-calcium phosphate, β-tricalcium phosphate, α-tricalcium phosphate, oxyapatite, or hydroxyapatite or mixtures thereof.

In some embodiments, at least 50%, at least 60%, at least 70%, at least 80%, at least 90%, at least 95% or all of the granules have a size range of between 50 microns and 500 microns. In some embodiments, at least 50%, at least 60%, at least 70%, at least 80%, at least 90%, at least 95% or all of the granules have a size range of between 50 microns and 100 microns. In some embodiments, at least 50%, at least 60%, at least 70%, at least 80%, at least 90%, at least 95% or all of the granules have a size range of between 100 microns and 200 microns. In some embodiments, at least 50%, at least 60%, at least 70%, at least 80%, at least 90%, at least 95% or all of the granules have a size range of between 200 microns and 300 microns. In some embodiments, at least 50%, at least 60%, at least 70%, at least 80%, at least 90%, at least 95% or all of the granules have a size range of between 300 microns and 400 microns. In some embodiments, at least 50%, at least 60%, at least 80%, at least 90%, or all of the granules have a size range of between about 400 microns and about 500 microns.

In some embodiments, at least 50%, at least 60%, at least 70%, at least 80%, at least 90%, at least 95% or all of the granules have a size range of between 500 microns and 3 mm. In some embodiments, at least 50%, at least 60%, at least 70%, at least 80%, at least 90%, at least 95% or all of the granules have a size range of between 500 microns and 1 mm. In some embodiments, at least 50%, at least 60%, at least 70%, at least 80%, at least 90%, at least 95% or all of the granules have a size range of between 1 mm and 2 mm. In some embodiments, at least 50%, at least 60%, at least 70%, at least 80%, at least 90%, at least 95% or all of the granules have a size range of between 2 mm and 3 mm.

As persons of ordinary skill in the relevant art are aware, hydroxyapatite is the major natural building block of bone and teeth. Typically, hydroxyapatite has a calcium to phosphate ratio of approximately 1.67, which is generally the same as the calcium to phosphate ratio in natural bone structures.

In some embodiments, in the relative weight percentages of the solid components are between about 70 wt % and about 80 wt % of ceramic particles and between about 20 wt % and about 30 wt % polysaccharide excipients. In some embodiments, the relative weights of the solid components may be between about 60 wt % and about 90 wt % of ceramic particles and between about 10 wt % and about 40 wt % polysaccharide excipients. In some embodiments, the relative weights of the solid components may be between about 60 wt % and about 70 wt % of ceramic particles and between about 30 wt % and about 40 wt % polysaccharide excipients. In some embodiments, the relative weights of the solid components may be between about 80 wt % and about 90 wt % of ceramic particles and between about 10 wt % and about 20 wt % polysaccharide excipients. Combined with these solid components may, for example, be a liquid such as phosphate buffer saline in an amount of about 1 milliliter of liquid per gram of solid to about 2.25 milliliters of liquid per gram of solid. In one exemplary embodiment, the relative amount of the solid components are biphasic calcium phosphate in an amount of about 70 weight percent of the solid material, alginate in an amount of about 30 weight percent of the solid material. A phosphate buffer saline may be present in an amount of about 1.5 milliliters per gram of solid components.

Table I below shows a range of weight percentages of the final implant according to some embodiments of the present invention:

TABLE I

| wt % of final implant (solid + liquid) | | |
| --- | --- | --- |
|  | Min | Max |
| Bicalcium phosphate buffer saline | 25% | 40% |
| Alginate | 5% | 15% |
| Phosphate buffer saline | 50% | 70% |

The bioactive agent, when present, may for example be a growth factor such as bone morphogenetic protein (e.g., BMP-1, BMP-2, BMP-3, BMP-4, BMP-5, BMP-6, BMP-7, BMP-8, BMP-9, BMP-10, BMP-11, BMP-12, BMP-13, BMP-14, BMP-15), and one or more different growth factors may be included in the implant. When including a growth factor, one may first manually mix the polysaccharide and granules and then soak the composition in a solution that comprises the growth factor. This resulting composition may be delivered to an end user as a pre-mixed formulation.

In some embodiments, the composition that will form the implant comprises collagen, such as Type I bovine collagen. In other embodiments there is an absence of collagen. Further, in some embodiments, the composition that will form the implant contains one or more non-collagenous fibrous components, such as hydroxybutyrate and/or a cross-linked alginate. These non-collagenous fibrous components may enhance osteoconductivity. In some embodiments the composition contains both crosslinked and non-crosslinked alginates. In other embodiments, the composition contains no alginates, only crosslinked alginates or only non-crosslinked alginates.

Additionally, in some embodiments, the compositions that will form the implants contain neither human nor animal tissue derived components. By omitting these types of components, the risk of disease transmission can be reduced, and particularly in embodiments that contain no collagen, the implants will be particularly advantageous for use in applications in which collagen containing products are prohibited.

In some embodiments, the compositions that will form the implants will also contain a liquid component such as water. As a practical matter, the composition that is to be shaped and implanted may be supplied to a provider in a ready to use formulation. For example, a composition that is to be molded to a desired implant shape may be prehydrated and supplied with a syringe or preloaded in a syringe. In some embodiments, hydration is accomplished with sterile water.

In some embodiments, the implant is designed to be flowable through a syringe as well as to be malleable and cohesive such that it may be intraoperatively shaped and molded to conform to a surgical site. Because these characteristics are present, a health care provider will have a longer time span in which to shape the implant for use in each application. Thus, the composition can be dispensed from the syringe, molded and then inserted by hand into a desired site.

The implant may be combined at an operative site with one or more of bone marrow aspirate, autograft tissue, allograft tissue and synthetic grafting agents. It also may be of use in a number of different locations, including but not limited to the spine, orthopedic sites, and COMF. In some embodiments, the implant of the present invention is particularly useful for filling of periodontal defects, filling of dental extraction sockets, filling of cystic defects, sinus lifts, alveolar ridge augmentation, oral or maxillofacial augmentation or reconstruction, interbody or posterior-lateral applications, non-loaded bearing defects, and voids caused by trauma. In these and other applications, the implant may be used with or without internal fixation.

The implants of the present invention are relatively easy to prepare. For example, one may take the putty composition and by hand or any mixing apparatus, work in the granules so that they are dispersed in the putty. For the user of the implant, the composition would typically come pre-mixed with the putty composition already having had the granules worked into them. Because of the composition of the implant, there is essentially no limit on the handling time or working time.

In some embodiments, the components of the composition of the implant are such that there is no setting time. Thus, in some embodiments there may be no stabilizers (also known as stabilizing agents). In other embodiments the implant may further contain a stabilizing agent, which may be a material that will allow a calcium phosphate mineral to set when reacted after the calcium phosphate has been stored for a predetermined amount of time. In some embodiments, this time period is at least one month, at least two months, at least three months, at least four months, at least five months, at least six months. In some embodiments, this time period is less than seven months, less than six months, less than five months, less than four months, less than three months, or less than two months.

Examples of the stabilizing agents that can be used in accordance with the present invention, include but are not limited to $MgO$, $MgO_2$, $Mg(OH)_2$, $MgHPO_4$, $MgHPO_4.3H_2O$, $MgHPO_4.7H_2O$, $Mg_3(PO_4)_2$, $Mg_3(PO_4)_2.4H_2O$, $Mg_3(PO_4)_2.8H_2O$, $Mg_3(PO_4)_2.22H_2O$, $MgCO_3$, $MgCO_3.3H_2O$, $MgCO_3.5H_2O$, $3MgCO_3$ $Mg(OH)_23H_2O$, $MgCO_3Mg(OH)_2.3H_2O$, $Mg(C_3H_5O_3)_2.3H_2O$, $MgC_2O_42H_2O$, $Mg(C_4H_4O_6)_2.4H_2O$, $MgCO_3CaCO_3$, $Mg_2P_2O_7$, $Mg(C_{12}H_{23}O_2)_22H_2O$, $Mg(C_{14}H_{27}O_2)_2$, $Mg(C_{18}H_{33}O_2)_2$, or $Mg(C_{18}H_{35}O_2)_2$ and/or a mixture thereof. In some embodiments the preferred stabilizing agent is magnesium oxide.

In some embodiments the stabilizing agent is present in an amount of from about 10 ppm to about 60 ppm or from about 30 pm to about 50 ppm or from about 35 ppm to about 45 ppm relative to the total weight of the calcium phosphate.

In some embodiments one or more of the following additives is included in addition to the growth factor referenced above or instead of the growth factor referenced above: proteins, X-ray opacifying agents, medicaments, supporting or strengthening filler materials, crystal growth adjusters, viscosity modifiers, pore forming agents and mixtures thereof.

The implant may also contain one or more antibiotics. Examples of antibiotics that may be used, include but are not limited to nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, teromyocin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol and any combination thereof.

The antibiotics may be integrated into the composition in the same way that, the growth factor is integrated into it. Further, an antibiotic may be included instead of or in addition to a growth factor.

Figure 2A:
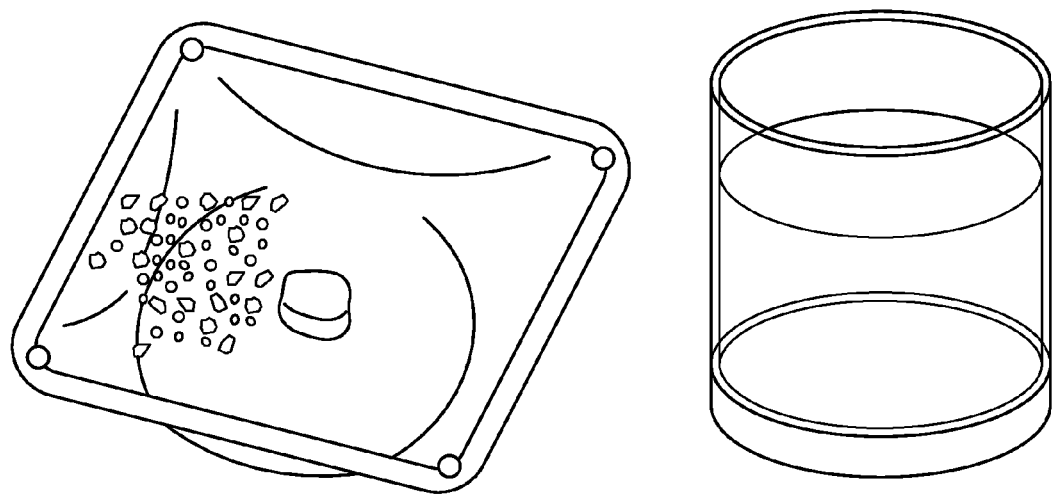
FIG. 2A is a representation of the implant of an embodiment of the present invention.
Figure 2B:
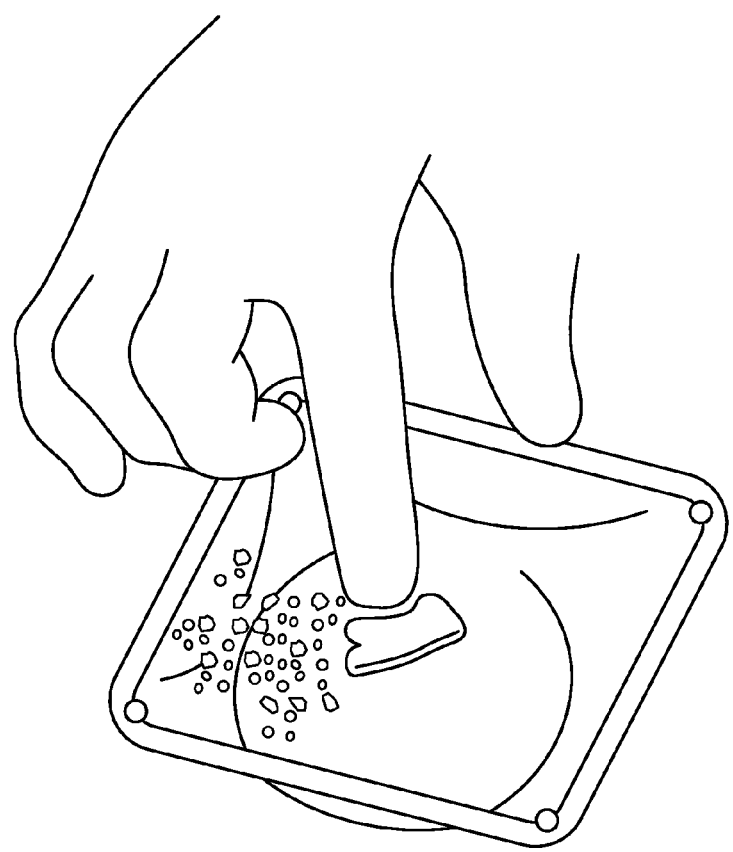
FIG. 2B is a representation of the same implant with its shape having been altered.

The accompany figures demonstrate the ease of working with the compositions that form the implants of the present invention. FIG. 1 shows the ease of dispensing the material that makes up the implant through a syringe FIG. 2A shows the cohesiveness of the implant in a wet environment. FIG. 2B shows the composition of the implant when being molded to a desired shape in a wet environment. As these figures show, the material remains cohesive when submerged and manipulated in a liquid.

Figure 3A:
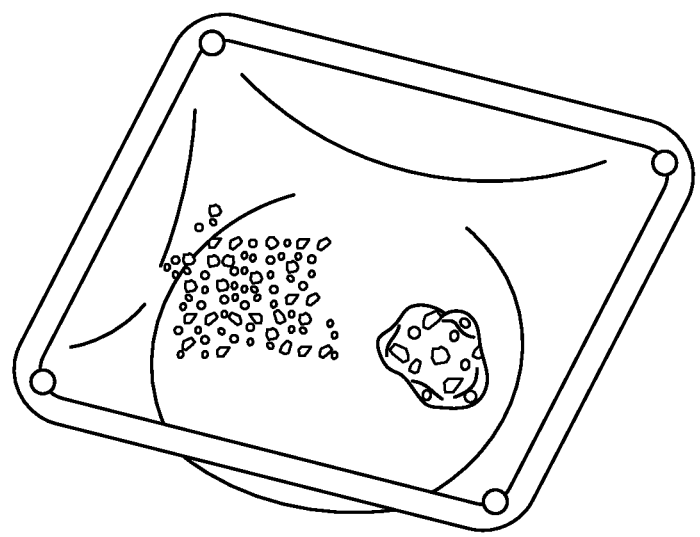
FIG. 3A is a representation of a putty and plurality of beads prior to having been combined.
Figure 3B:
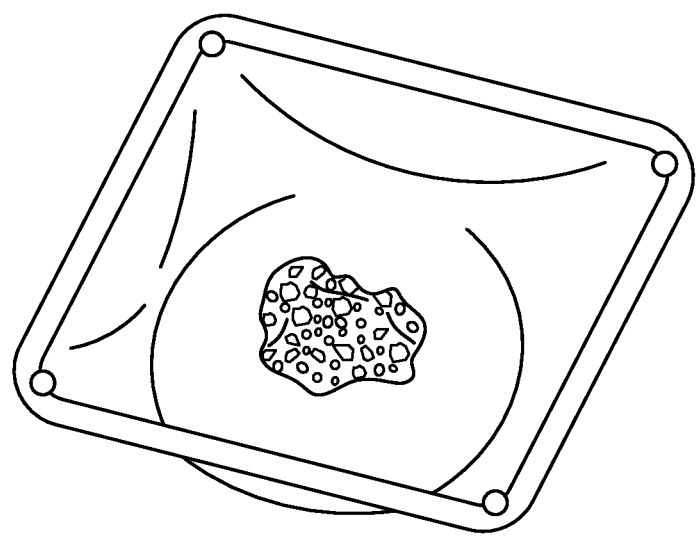
FIG. 3B is a representation of the putty and beads of FIG. 3A after having been combined.

FIG. 3A shows the polysaccharide/ceramic putty and additional granules prior to their combination. The additional granules simulate mixing with autograft bone. FIG. 3B shows the polysaccharide/ceramic putty and additional granules as combined. These figures demonstrate that the composition that is generated is cohesive.

Figure 4A:
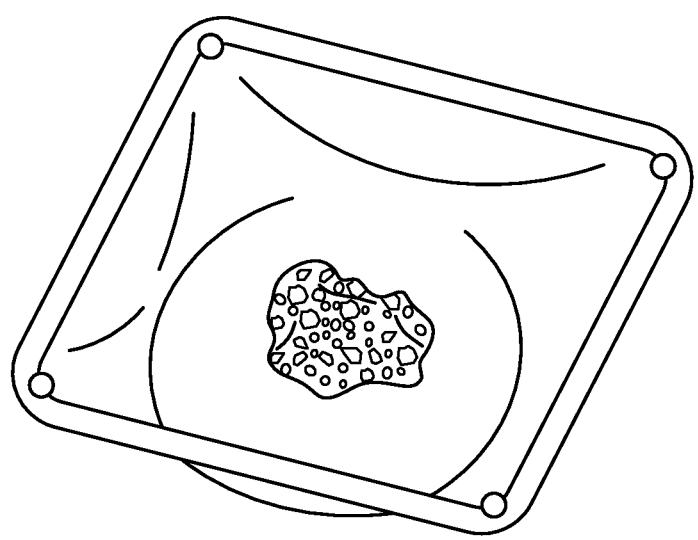
FIG. 4A is a representation of the implant of an embodiment of the present invention prior to having been molded to a desired shape.
Figure 4B:
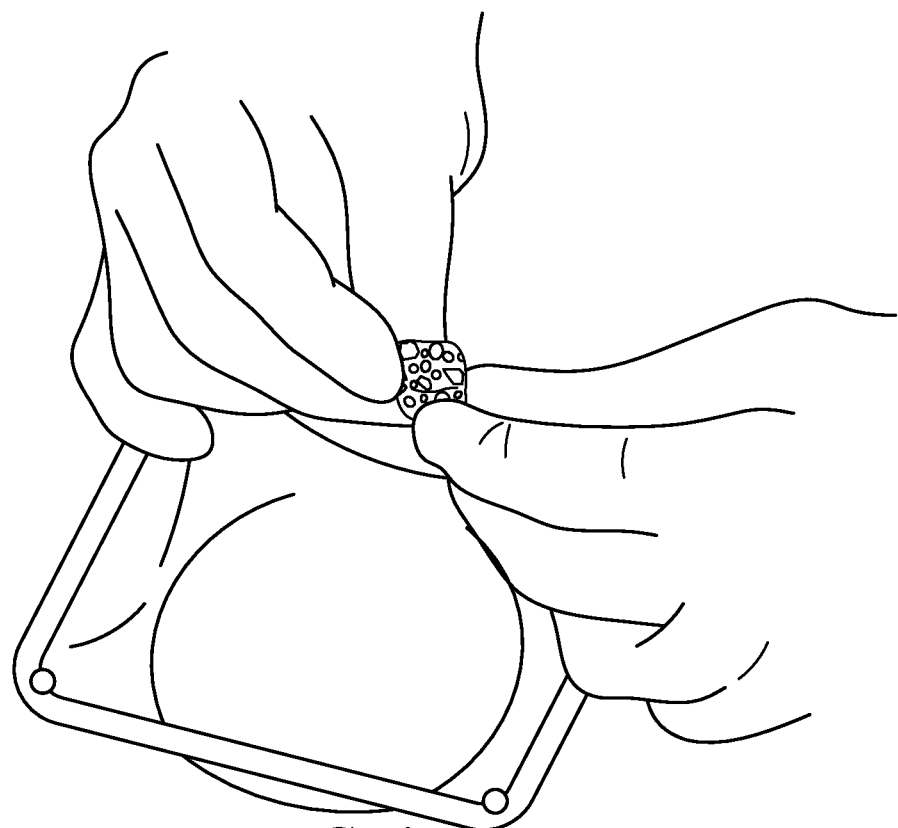
FIG. 4B is a representation of a person molding the composition of FIGS. 4A.
Figure 4C:
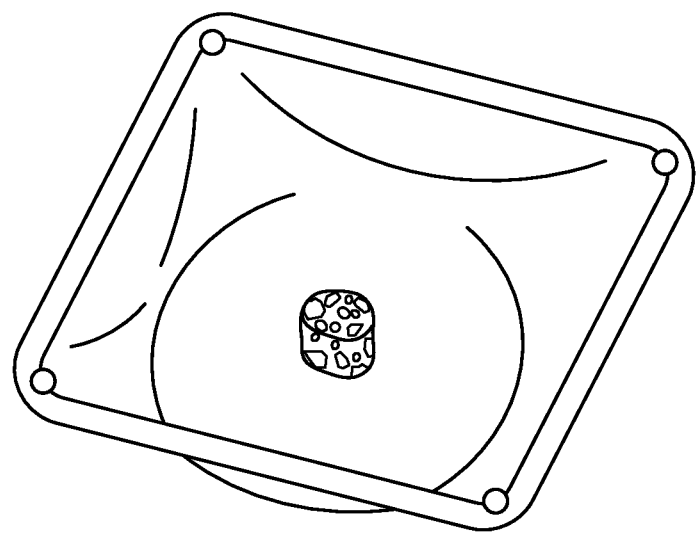
FIG. 4C is a representation of the composition of FIG. 4B after having been molded.

FIG. 4A shows the implant (polysaccharide/ceramic putty and additional granules to simulate autograft) in an unmolded state. FIG. 4B shows the composition of the implant being molded to a desired shape. FIG. 4C shows the composition in its final molded state.

As noted above, the composition may be supplied to a healthcare provider prehydrated with for example about 1.0 to about 2.25 ml of liquid per solid components. The liquid may for example, be water, saline or phosphate buffer saline or mixtures thereof.

After being implanted the polysaccharide will degrade first. For example, in some embodiments, at least 50%, at least 60%, at least 70%, at least 80%, at least 90%, at least 95% or all of the polysaccharide will degrade in a period of about 1-12 weeks, about 3-9 weeks, about 4-8 weeks, or about 5-7 weeks. This will leave the granules, which preferably, and as in the case of the calcium phosphate granules, are osteoconductive and able to induce cells to migrate into the area in which composition has been placed. Over time, e.g., about 6-15 months or about 9-12 months the granules may be resorbed, as the new bone material is grown by the body.

When the composition is in a putty form, it may be stored or placed into an open end syringe and then dispersed to a desired location (e.g., a preparation site or directly in a bone void) by a healthcare provider. When the composition is in a flowable state, a healthcare provider may chose to use a larger size needle or a small cannula.

What is claimed is:

1. A composition for filling an osseous void comprising:
   one or more non-cross-linked alginates comprising about 5% to about 15% of the composition;
   at least one of the following stabilizing agents: $MgO$, $MgO_2$, $Mg(OH)_2$, $MgHPO_4$, $MgHPO_4.3H_2O$, $MgHPO_4.7H_2O$, $Mg_3(PO_4)_2$, $Mg_3(PO_4)_2.4H_2O$, $Mg_3(PO_4)_2.8H_2O$, $Mg_3(PO_4)_2.22H_2O$, $MgCO_3$, $MgCO_3.3H_2O$, $MgCO_3.5H_2O$, $3MgCO_3Mg(OH)_2.3H_2O$, $MgCO_3Mg(OH)_2.3H_2O$, $Mg(C_3H_5O_3)_2.3H_2O$, $MgC_2O_4.2H_2O$, $Mg(C_4H_4O_6)_2.4H_2O$, $MgCO_3CaCO_3$, $Mg_2P_2O_7$, $Mg(C_{12}H_{23}O_2)_2.2H_2O$, $Mg(C_{14}H_{27}O_2)_2$, $Mg(C_{18}H_{33}O_2)_2$, $Mg(C_{18}H_{35}O_2)_2$, or a mixture thereof, wherein the stabilizing agent is present in an amount of from about 10 ppm to about 60 ppm; and
   a plurality of ceramic granules having a size range of between 2 mm and 3 mm, wherein the composition is free of collagen, the composition being moldable and adaptable to fill an osseous void on implantation, and wherein the composition remains moldable after implantation.

2. A composition of claim 1, wherein the ceramic granules comprise calcium phosphate.

3. A composition of claim 2, wherein the calcium phosphate is biphasic calcium phosphate.

4. A composition of claim 3, wherein the biphasic calcium phosphate consists of about 15 percent hydroxyapatite and about 85 percent beta-tricalcium phosphate.

5. A composition of claim 3, wherein the biphasic calcium phosphate is present in an amount of from about 25 wt % to about 40 wt % of the total composition; and the composition comprises phosphate buffered saline from about 50 wt % to about 70 wt % of the total composition.

6. A composition of claim 1, wherein the plurality of ceramic granules are beads.

7. A composition of claim 1 further comprising a non-collagenous fibrous component.

8. A composition of claim 7, wherein the non-collagenous fibrous component is hydroxybutyrate.

9. A composition of claim 7, wherein the non-collagenous fibrous component is a cross-linked alginate.

10. A composition of claim 2, further comprising a non-collagenous fibrous component.

11. A composition of claim 10, wherein the non-collagenous fibrous component is hydroxybutyrate.

12. A composition of claim 10, wherein the non-collagenous fibrous component is a cross-linked alginate.

13. A composition of claim 1 further comprising a growth factor.

14. A composition of claim 13, wherein the growth factor is a bone morphogenic protein (BMP).

15. A composition of claim 7 further comprises a growth factor.

16. A composition of claim 9 further comprises a growth Factor.

17. A composition of claim 16, wherein the growth factor is a bone morphogenic protein (BMP).

* * * * *